United States Patent [19]

Sivam

[11] Patent Number: 4,906,452
[45] Date of Patent: * Mar. 6, 1990

[54] TRICHOTHECENE CONJUGATES AND METHODS OF USE

[75] Inventor: Gowsala Sivam, Edmonds, Wash.

[73] Assignee: Neorx Corporation, Seattle, Wash.

[*] Notice: The portion of the term of this patent subsequent to May 17, 2005 has been disclaimed.

[21] Appl. No.: 187,113

[22] Filed: Apr. 28, 1988

Related U.S. Application Data

[63] Continuation-in-part of Ser. No. 788,325, Oct. 17, 1985, Pat. No. 4,744,981.

[51] Int. Cl.[4] .............................. A61K 39/395
[52] U.S. Cl. .............................. 424/10; 424/85.91; 424/85.8; 514/2; 530/387; 530/388; 530/402
[58] Field of Search .............. 424/85, 10, 85.91; 530/387, 388, 402

[56] References Cited

U.S. PATENT DOCUMENTS

| | | |
|---|---|---|
| 4,507,234 | 3/1985 | Kato et al. |
| 4,618,585 | 10/1986 | Chan |
| 4,624,846 | 11/1986 | Goldenberg |
| 4,744,981 | 5/1988 | Pa vanasasivam ............ 530/389 |

FOREIGN PATENT DOCUMENTS 088695  9/1983  European Pat. Off.

OTHER PUBLICATIONS

F. S. Chu et al., *Chem. Abstr.* 101:228260z (1984).
K. W. Hunter, Jr. et al., *Chem. Abstr,* 102:76957n (1985).
J. R. Bamburg, *Prog. Molec. Subcell, Biol.* 8:41–110 (1983).
J. W. Uhr, *J. Immunol.* 133:i–x (1984).
B. M. J. Foxwell, *Immunotoxicology,* Academic Press, London, pp. 359–368 (1983).
"Protection Against Trichothecene Mycotoxins", National Academy Press, Washington, D.C., pp. 17–20; 129–136 (1983).

*Primary Examiner*—Sam Rosen
*Attorney, Agent, or Firm*—Debra Leith

[57] ABSTRACT

Conjugates of trichothecenes and agents that bind to a defined population of cells are disclosed. Preferred are conjugates of trichothecene molecules with polyclonal or monoclonal antibodies or fragments thereof that recognize antigens that are present only on tumor cells or are augmented in their expression on tumor cells as compared to normal tissues. Trichothecene molecules are coupled to the agent through non-covalent and covalent linkages, such as peptide bonds, disulfide bonds, thioester bonds, or thioether bonds. Methods for reducing intoxification in a recipient of a trichothecene and an agent and for producing a trichothecene conjugate with improved solubility are also disclosed.

7 Claims, No Drawings

TRICHOTHECENE CONJUGATES AND METHODS OF USE

CROSS REFERENCE TO RELATED APPLICATION

This application is a continuation-in-part application to Ser. No. 788,325, filed Oct. 17, 1985, which issued May 17, 1988 as U.S. Pat. No. 4,744,981.

DESCRIPTION

1. Technical Field

The present invention relates generally to the conjugation of molecules to agents that bind to a defined population of cells, and more specifically, to conjugates of agents such as antibodies with trichothecenes and to methods for using these conjugates.

2. Background of the Invention

The use of antibodies as carriers for toxic agents to kill tumor cells selectively has depended upon the coordination of research in three distinct areas: (a) the development of polyclonal or monoclonal antibodies (and their fragments) with specificity for a defined population of cells, such as tumor cells; (b) the elucidation of the chemistry of toxic molecules and the conditions appropriate for their linkage to antibodies; and (c) the production and isolation of naturally occurring toxic molecules. Conjugates of monoclonal antibodies with drugs, plant toxins, and ribosomal inactivating proteins have been summarized by Morgan and Foon, (Monoclonal Antibody Therapy of Cancer: Preclinical Models and Investigations; *Basic and Clinical Tumor Immunology, Vol.* 2, Kluwer Academic Publishers, Hingham, MA) and Uhr (*Journal of Immunology* 133: i–vii, 1984). Interest in the potent higher plant toxic molecules peaked with the development of monoclonal antibodies, because it appeared that the latter could be used as highly specific targeting agents for these toxins.

In general, the higher molecular weight toxins have characteristic A and B chains, with the B chain responsible for binding (usually via lectins to oligosaccharides) and A chains that act catalytically to irreversibly inhibit elongation factor 2 (EF2), therefore preventing protein synthesis. The vision was that the specificity of the antibody could substitute for the nonspecific binding of B chain and deliver A chain selectively to tumor cells. More recently, a class of compounds called "ribosomal inactivating proteins" (RIPs) have been discovered that represent the equivalent of A chains without any associated B chain.

A number of obstacles emerged, however, that compromised the realization of this simple vision. First, it was apparent that it was critical to develop systems to remove B chain from A chain beyond purity achieved with simple affinity chromatography. The RIPs and cloned toxins represent one practical solution to this problem. Second, the reticuloendothelial system removes macromolecules from the circulation, especially those that have been altered, such as an antibody that has been bound to toxin. Third, it became apparent that there were receptors for the carbohydrates that exist naturally on the protein plant toxins. These also contributed to nonspecific uptake and, therefore, toxicity. Finally, it became clear that B chain was critical for more than just binding to the cell, and seemed to facilitate the translocation of the A chain into the cell and eventually into the cytoplasm, where it effected its cytotoxicity.

Due to these obstacles, there is a need in the art for a class of conjugates that overcome the problems noted above, while concurrently possessing the capability of killing defined populations of cells, such as tumor cells, on a selective basis. The present invention fulfills this need and further provides other related advantages.

DISCLOSURE OF THE INVENTION

Briefly stated, the present invention discloses conjugates of trichothecenes and agents that are capable of specifically binding to a defined population of cells. Preferred are conjugates of trichothecene molecules with polyclonal or monoclonal antibodies or fragments thereof that recognize antigens that are present only on tumor cells or are augmented in their expression on tumor cells as compared to normal tissues.

In accordance with the present invention, "trichothecenes" are defined to include molecules derived from *Fungi imperfecti, Baccharus megapotamica,* or prepared synthetically or synthesized from fungal products that have as their common characteristic a sesquiterpenoid central ring structure, and simple and macrocyclic trichothecene derivatives.

The trichothecenes molecules are coupled to the agent through non-covalent and covalent linkages, such as a peptide bond, a disulfide bond, a thioester bond, or a thioether bond. This covalent linkage may be formed between: (a) the trichothecene itself; (b) a trichothecene hemisuccinate carboxylic acid; (c) a trichothecene hemisuccinate N-hydroxy succinimidate ester; or (d) trichothecene complexes with poly-L-lysine or any polymeric carrier; and one or more amino, sulfhydryl or carboxyl groups of the agent.

A related aspect of the present invention is directed toward a method for inhibiting the growth and metabolism of antigen positive cells, comprising exposing the antigen positive cells to a conjugate of a trichothecene and an agent that is capable of specifically binding to the antigen positive cells.

An additional aspect of the present invention discloses a method for rendering relatively insoluble trichothecene conjugates soluble, by glycosylation.

Other aspects of the invention will become relevant upon reference to the following detailed description.

DETAILED DESCRIPTION OF THE INVENTION

"Trichothecenes" are a species of mycotoxins produced by soil fungi of the class *Fungi imperfecti* or isolated from *Baccharus megapotamica* (Bamburg, J. R., *Proc. Molec. Subcell. Bio.* 8: 41–110, 1983; Jarvis & Mazzola, *Acc. Chem. Res.* 15: 338–395, 1982). They appear to be the most toxic molecules that contain only carbon, hydrogen and oxygen (Tamm, C. *Fortschr. Chem. Org. Naturst.* 31: 61–117, 1974). They all act at the level of the ribosome as inhibitors of protein synthesis, either at the initiation, elongation or termination phases. In the formulation of the present invention, it was found that as small molecules (ca. 4–600 m.w.) they have potential advantages:

(1) improved delivery due to only minor changes in the molecular weight of antibody;
(2) lack of receptor mediated, nonspecific uptake, e.g., via carbohydrate receptors, a drawback of higher molecular weight (ca. 30,000 m.w.) plant toxins, like ricin A chain, or ribosomal inactivating proteins such as gelonin.

Similar to toxins, however, mycotoxins can be extremely potent. They are the most potent small molecule inhibitors of protein synthesis in eucaryotic cells. Unconjugated to antibody, verrucarin A (Table 4) is 10-fold or greater more potent than actinomycin D, the most potent per weight of the chemotherapeutic drugs currently approved for clinical use. Since most currently used drugs act at the level of DNA, these ribosomal inactivating drugs, like toxins, should not be adversely affected by resistance to "standard" drugs, and should produce additive cytotoxicity to existing therapies.

There are two broad classes of trichothecenes: those that have only a central sesquiterpenoid structure and those that have an additiional macrocyclic ring (simple and macrocyclic trichothecenes, respectively). The simple trichothecenes may be subdivided into three groups. Group A simple trichothecenes may be characterized by the formula:

wherein
$R_1$ is H, OH, or $$O-\overset{O}{\underset{\|}{C}}-CH_3;$$

$R_2$ is H, OH, or $$O-\overset{O}{\underset{\|}{C}}-CH_3;$$

$R_3$ is H, OH, or $$O-\overset{O}{\underset{\|}{C}}-CH_3;$$

$R_4$ is H or OH; and
$R_5$ is H, OH, $$O-\overset{O}{\underset{\|}{C}}-CH_3, \text{ or } \overset{O}{\underset{\|}{C}}-O-CH_2CH(CH_3)_2.$$

Representative Group A simple trichothecenes and corresponding functional groups are listed in Table 1.

TABLE 1

| Group A Simple Trichothecenes | | | | | |
|---|---|---|---|---|---|
| Trichothecenes | $R_1$ | $R_2$ | $R_3$ | $R_4$ | $R_5$ |
| Trichothecene (scirpene) | H | H | H | H | H |
| Trichodermol (roridin C) | H | OH | H | H | H |
| Dihydrotrichothecene | H | H | OH | H | OH |
| Scirpen-4, 8-diol | H | OH | H | H | OH |
| Verrucarol | H | OH | OH | H | H |
| Scirpentriol | OH | OH | OH | H | H |
| T-2 tetraol | OH | OH | OH | H | OH |
| Pentahydroxyscirpene | OH | OH | OH | OH | OH |
| 4-Deacetylneosolaniol | OH | OH | OH | H | OH |
| Trichodermin | H | OAc | H | H | H |
| Deacetylcalonectrin | OAc | H | OH | H | H |

TABLE 1-continued

| Group A Simple Trichothecenes | | | | | |
|---|---|---|---|---|---|
| Trichothecenes | $R_1$ | $R_2$ | $R_3$ | $R_4$ | $R_5$ |
| Calonectrin | OAc | H | OAc | H | H |
| Diacetylverrucarol | H | OAc | OAc | H | H |
| 4-Monoacetoxyscirpenol | OH | OAc | OH | H | H |
| 4, 15-Diacetoxyscirpenol (DAS) | OH | OAc | OAc | H | H |
| 7-Hydroxydiacetoxyscirpenol | OH | OAc | OAc | OH | H |
| 8-Hydroxydiacetoxyscirpenol (neosolaniol) | OH | OAc | OAc | H | OH |
| 7, 8-Dihydroxydiacetoxyscirpenol | OH | OAc | OAc | OH | OH |
| 7-Hydroxy-8-acetyldiacetoxyscirpenol | OH | OAc | OAc | OH | OAc |
| 8-Acetylneosolaniol (8-Acetyl-DAS) | OH | OAc | OAc | H | OAc |
| NT-1 | OH | OAc | OH | H | OAc |
| NT-2 | OH | OAc | OH | H | OH |
| HT-2 toxin | OH | OH | OAc | H | OCOCH$_2$—CH(CH$_3$)$_2$ |
| T-2 toxin | OH | OAc | OAc | H | OCOCH$_2$—CH(CH$_3$)$_2$ |
| Acetyl T-2 toxin | OAc | OAc | OAc | H | OCOCH$_2$—CH(CH$_3$)$_2$ |

Group B simple trichothecenes may be characterized by the formula:

wherein
$R_1$ is H, OH, or $$O-\overset{O}{\underset{\|}{C}}-CH_3;$$

$R_2$ is H, OH, or $$O-\overset{O}{\underset{\|}{C}}-CH_3 \text{ or } O-\overset{O}{\underset{\|}{C}}-CH=CH-CH_3;$$

$R_3$ is H, OH, or $$O-\overset{O}{\underset{\|}{C}}-CH_3;$$

and
$R_4$ is H, OH, or $$O-\overset{O}{\underset{\|}{C}}-CH_3.$$

Representative Group B simple trichothecenes and corresponding functional groups are listed in Table 2.

TABLE 2

| Group B Simple Trichothecenes | | | | |
|---|---|---|---|---|
| Trichothecenes | $R_1$ | $R_2$ | $R_3$ | $R_4$ |
| Trichothecolone | H | OH | H | H |
| Trichothecin | H | OCOCH= | H | H |

TABLE 2-continued

Group B Simple Trichothecenes

| Trichothecenes | $R_1$ | $R_2$ | $R_3$ | $R_4$ |
|---|---|---|---|---|
| | | $CHCH_3$ | | |
| Deoxynivalenol (DON) | OH | H | OH | OH |
| 3-Acetyldeoxynivalenol | OAc | H | OH | OH |
| 5-Acetyldeoxynivalenol | OH | H | OH | OAc |
| 3, 15-Diacetylde-oxynivalenol | OAc | H | OAc | OH |
| Nivalenol | OH | OH | OH | OH |
| 4-Acetylnivalenol (fusarenon-X) | OH | OAc | OH | OH |
| 4,15-Diacetylnivalenol | OH | OAc | OAc | OH |
| 4,7,15-Triacetylnivalenol | OH | OAc | OAc | OAc |
| Tetracetylnivalenol | OAc | OAc | OAc | OAc |

Group C simple trichothecenes may be characterized by the formula:

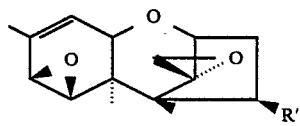

wherein R' is OH or

Representative Group C simple trichothecenes and corresponding R' functional groups are listed in Table 3.

TABLE 3

Group C Simple Trichothecenes

| Trichothecenes | R' |
|---|---|
| Crotocol | OH |
| Crotocin | $OCOCH=CHCH_3$ |

The macrocyclic trichothecenes may be characterized by the formula:

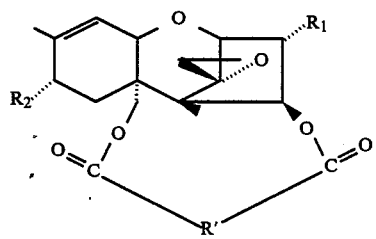

wherein
$R_1$ is OH or

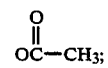

$R_2$ is H, OH,

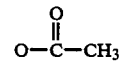

or $OCOCH_2CH(CH_3)_2$; and
R' is:

TABLE 4

| R' | Representative Macrocyclic Trichothecenes |
|---|---|
| $-CHOHCHMeCH_2CH_2O\overset{O}{\overset{\|}{C}}CH=CHCH=CH-$ | Verrucarin A |
| $-\underset{\underset{O}{\diagdown\diagup}}{CHCMeCH_2CH_2}O\overset{O}{\overset{\|}{C}}CH=CHCH=CH-$ | Verrucarin B |
| $-CH=CMeCH_2CH_2O\overset{O}{\overset{\|}{C}}CH=CHCH=CH-$ | Verrucarin J (Satratoxin C) |
| $-\overset{O}{\overset{\|}{C}}CHMeCH_2CH_2O\overset{O}{\overset{\|}{C}}CH=CHCH=CH-$ | 2-Dehydro-verrucarin A |
| $-CHOHCHMeCH_2CH_2OCHCH=CHCH=CH-$<br>$\quad\quad\quad\quad\quad\quad\quad\quad\quad\quad\quad\; \|$<br>$\quad\quad\quad\quad\quad\quad\quad\quad\quad\quad\; MeCHOH$ | Roridin A |
| $-\underset{\underset{O}{\diagdown\diagup}}{CHCMeCH_2CH_2}OCHCH=CHCH=CH-$<br>$\quad\quad\quad\quad\quad\quad\quad\quad\quad\quad\; \|$<br>$\quad\quad\quad\quad\quad\quad\quad\quad\quad\; MeCHOH$ | Roridin D |
| $-CH=CMeCH_2CH_2OCHCH=CHCH=CH-$<br>$\quad\quad\quad\quad\quad\quad\quad\quad\quad\quad\; \|$<br>$\quad\quad\quad\quad\quad\quad\quad\quad\quad\; MeCHOH$ | Roridin E (Satratoxin D) |

TABLE 4-continued

| R' | Representative Macrocyclic Trichothecenes |
|---|---|
| —CH=CHMeCH₂CH(O-O)CH=CHCH=CHCH— with Me on the dioxolane | Roridin H |
| —HC(O-)(OH) ring with —CH=CHCH=CH— and CHOCH₃ substituent | Satratoxin F |
| —HC(O-)(OH) ring with —CH=CHCH=CH— and CH(CH₃)OH substituent | Satratoxin G |
| —CH= with pyran ring (OH), —CH=CHCH=CH—, CH(CH₃)OH | Satratoxin H |
| —CH= with pyran ring, CH₂CH₂CH=CH—, H, OH, OH | Vertisporin |
| HC(O-)(O-) ring, OH (ax), (C=O)—CH₃CH₂CH₂CH=CH | Mytoxin A |
| HC(O-)(O-) ring, OH (eq), (C=O)—CH₃CH₂CH₂CH=CH | Mytoxin C |
| —CH= with ring, OH (ax), (C=O)—CH₃CH₂CH₂CH=CH | Mytoxin B |
| HC(O-)(O-) ring, OH (ax), =CHCH₂CH=CH— | If R₂ = H  Myrotoxin A<br>If R₂ = OAc  Myrotoxin B |
| HC(O-)(O-) ring, OH (eq), —CHCH₂CH=CH— | If R₂ = H  Myrotoxin C<br>If R₂ = OAc  Myrotoxin D |

TABLE 4-continued

| R' | Representative Macrocyclic Trichothecenes |
|---|---|
| (structure) | Roritoxin A |
| (structure) | Roritoxin B |
| (structure) | Roritoxin D. |

The macrocyclic trichothecenes may also be characterized by the formula:

(structure)

wherein
$R_1$ is: H, OH, or $$O=C-CH_3;$$

$R_2$ is: H, OH, $$O-C-CH_3$$

or $OCOCH_2CH(CH_3)_2$; and
R' is:

(structure)

Roritoxin C; or $$\underset{O}{\overset{}{\diagup}} C(CH_3)CH(OH)CH_2OCHCH=CHCH=CH- \\ \overset{|}{MeCH(OH)} \quad \text{(Baccharins)}.$$

In addition to the general structure shown above, many "baccharins" have been isolated from the higher plant *Baccharis megapotamica*, and are described in the literature, for instance as disclosed by Jarvis et al. (Chemistry of Alleopathy, ACS Symposium Series No. 268; ed. A. C. Thomspon, 1984, pp. 149-159).

The sesquiterpenoid ring functions in a manner similar to the A chains of plant toxins, in binding to ribosomes and inhibiting protein synthesis. The macrocyclic ring enhances cell binding and internalization in an unknown manner. There are molecules in each class that, while potent inhibitors of translation in cell-free systems, are only minimally cytotoxic ($ID_{50}=10$ ug/ml) to eucaryotic cells.

Variations in ribosome binding ability are not well correlated with cytotoxicity, strongly suggesting that differential delivery to ribosomes in the cell or intracellular deactivation may play an important role in the activities of these drugs against eucaryotic cells. (Bamburg, J. R., Biological and Biochemical Actions of Trichothecene Mycotoxins, *Prog. Mol. Subcell. Biol.* 8: 41-110, 1983; McLaughlin, C. S., Vaughan, M. H., Cambell, I. M., Wei, C. M., Stafford, M. E., and Hansen, B. S., Inhibition of Protein Synthesis by Trichothecenes, In: *Mycotoxins in Human and Animal Health*, Pathotox Publishers, Park Forest South, IL, pp. 263-273, 1977; and Doyle, T. W., and Bradner, W. T., Trichothecenes, In: *Anticancer Agents Based on Natural Product Models* [Cassidy and Bouros, eds.] Academic Press, Inc., New York, NY, pp. 43-72, 1980.) It is possible, for example, that verrucarol binds poorly to cell membranes, or may be deactivated intracellularly, deficiencies that may be overcome by conjugation to monoclonal antibodies. There have been some studies of the rates at which certain of the trichothecenes are converted into biologically inactive molecules (apotrichothecenes) by intracellular acid catalysis as might occur in lyzosomes. The macrocyclic trichothecenes and some simple trichothecenes, such as anguidine and T-2 toxin, are inactivated quite slowly, whereas less cytotoxic molecules, such as verrucarol, are inactivated more quickly. There is an inverse linear correlation between cytotoxicity and the rate of this rearrangement into apotrichothecenes.

Anguidine, a simple trichothecene, has been tested in Phase I (Murphy, W. K., Burgess, M. A., Valdivieso, M., Livingston, R. B., Bodey, G. P., and Freireich, E. J., Phase I Evaluation of Anguidine, *Cancer Treat. Repts.* 62: 1497, 1978) and Phase II (Adler, S. S., Lowenbraun, S., Birch, B., Jarrell, R., and Garrerd, J., Anguidine: A Broad Phase II Study of the Southeastern Cancer Study Group, *Cancer Treat. Repts.* 68: 423, 1984) clinical trials in patients. The overall tumor response rate was low and there was considerable hematologic toxicity in the Phase II trial. In the Phase I trial, toxicity included nausea, vomiting, hypotension, central nervous system symptoms, diarrhea, chills and fever, generalized burning erythema, stomatitis, shortness of breath, moderate myelosuppression with an association between life threatening toxicity and the presence of liver metastases or impairment of liver function recognized at higher doses.

The linkage of trichothecene molecules to polyclonal and monoclonal antibodies or fragments thereof that recognize antigens that are augmented in their expression on tumor cells as compared to normal tissues may be divided into two distinct strategies: (1) linking poorly cytotoxic trichothecenes to antibodies or fragments thereof in order to render them cytotoxic; and (2) conjugating cytotoxic trichothecenes to antibodies or fragments thereof to deliver them selectively to tumor cells, sparing normal tissues most of their toxicity.

Within the present invention, monoclonal antibodies were prepared by immunizing rodents or other animals and/or are developed by harvesting human lymphocytes from patients bearing malignancies and immortalizing the antibody secretion of the cells by standard hybridoma technology (Geffer et al., *Somatic Cell Genet.* 3: 231, 1977). Alternatively, polyclonal antiserum is prepared by harvesting serum from animals following immunization with tumor cells or other defined tumor-associated antigens or harvesting from humans who have or have had exposure to tumors or tumor-associated antigens, and subjecting the serum to standard purification techniques. Antibodies were screened for specificity using standard radioimmunoassay or enzyme-linked immunosorbent assay (ELISA) against the appropriate targets. Screening was performed with normal human tissues to select antibody with appropriate tumor specificity.

After purification of the desired antibody species, the antibodies were conjugated to derivatized trichothecene molecules through the use of linking molecules. The carboxylic acid of the trichothecene hemisuccinate was reacted with a carbodiimide reagent and linked to an amino group of the antibody. Alternatively, an N-succinimidyl ester of the trichothecene hemisuccinate is prepared and is used to link derivatized tricothecene to the amino groups of the antibody. Both of these methods result in an amide bond between the trichothecene and the antibody. Trichothecenes that possess a free hydroxyl group may be directly linked to an antibody molecule using reaction with a carbodiimide. Thioether linkage can also be used as a stable bond between the antibody and the trichothecene. When a more labile bond seems desirable, the trichothecene may be linked by a disulfide or a thioester bond to the antibody.

In addition, the trichothecene-antibody conjugates (immunoconjugates) may be formed using "spacer arms" and/or carrier molecules. Suitable spacer arm groups include amino acids, saccharides, proteins, methylene ($-CH_2-$), methyleneoxy ($-CH_2-O-$), methylenecarbonyl ($-CH_2-CO-$), and combinations thereof. The amino acid, or saccharide, spacer arm may be an individual amino acid, or saccharide, or homo- or heteropolymers thereof. For example, the trichothecene molecule may be linked to poly-L-lysine (m.w. 300 to 150,000). The poly-L-lysine/trichothecene complex may then be linked to the antibody via an amide bond. Suitable carrier molecules include proteins, such as serum albumins. An advantage of a carrier is that an immunoconjugate may be formed which is capable of delivering greater amounts of a toxic substance.

The immunoconjugates produced were easily separated from the unreacted trichothecene by fast protein liquid chromatography (FPLC) gel filtration using a TSK 3000 column. Alternatively, the unreacted trichothecene is removed by dialysis.

The molecular weight of the conjugate may not be significantly greater than that of the free antibody. Therefore, separation of the immunoconjugate from free antibody may require use of hydroxylapatite or hydrophobic column chromatography.

Conjugates were analyzed by isoelectric focusing (IEF) and SDS-PAGE. IEF is a measure of the degree of substitution and resulting charge of the antibody. SDS-PAGE separates proteins on the basis of molecular weight and is used to assess the covalent aggregates formed during the conjugation process. The conjugate is compared to the unconjugated antibody for immune reactivity that is quantified by flow cytometry. The immunoconjugates are incubated with antigen positive cells, washed, and then the cells are incubated with fluorescein isothiocyanate-linked goat anti-mouse antibody. Cell-bound fluorescence is read on a flow cytometer and mean fluorescence index is calculted. Competition is performed using a standard unconjugated antibody preparation in comparison for inhibition with the conjugate. Similar analyses, employing antigen negative cells, were used to demonstrate the retention of specificity of the conjugate for antigen positive cells.

Cytotoxicity of the immunoconjugates was assessed with two methods. A colorimetric assay employs 3-(4,5-dimethylthiazol-2-yl)-2,5-diphenyl tetrozolium bromide as the substrate. This substance is cleaved by living cells to yield a dark-blue formazan product. This process requires active mitochondria. The substrate (MTT) was solubilized and read on an ELISA reader. This assay has an excellent correlation with the standard $^3H$-thymidine incorporation assay and avoids the use of radioactivity. $^3H$-thymidine was reserved for confirmation of major results.

Potency and selectivity assays were performed by incubating conjugates with antigen positive and antigen negative cell lines. Conjugates were added to the cells at varying concentrations and cell survival assessed after continuous and short exposure times. The conjugates were incubated with the cells for three days for continuous exposure and for two hours for the short exposure. At the end of three days cell survival was assessed.

The conjugates were also tested for their ability to inhibit peptidyl transferase. The assay is based upon competition with radiolabeled trichodermin for the binding site on the 60S ribosome. Conjugates were also tested for their ability to inhibit protein synthesis using natural mRNA to determine their overall effect on protein synthesis and a poly U to measure the effect on elongation.

A related aspect of the present invention provides a method for rendering relatively insoluble trichothecene conjugates soluble by glycosylation. The method comprises the steps of glycosylating a trichothecene to form a glycosylated trichothecene and conjugating the glycosylated trichothecene to an antibody or antibody fragment that is capable of specifically binding to a defined population of cells, thereby forming the trichothecene conjugate with improved solubility.

The following examples are offered by way of illustration and not by way of limitation.

EXAMPLE I

Verrucarol

Verrucarol is a simple, poorly cytotoxic trichothecene. It is conjugated to anti-melanoma monoclonal antibody 9.2.27 using a carbodiimide. More specifically, antibody (10 mg) in 2 ml of 0.1M NaCl was mixed with 5 mg of trichothecene (in 0.1 ml of DMSO and 1 ml of 0.1M sodium phosphate buffer, pH 6.0) and 30 mg of 1-ethyl-3,3-dimethylamino-propyl-carbodiimide. The mixture was stirred at room temperature for 24 hours. After reaction, the solution was dialyzed against 0.1M sodium phosphate, pH 7.0.

Primary or secondary hydroxyl groups of the trichothecene molecule react with the carbodiimide to form derivatized tricothecene. This derivatized trichothecene molecule then reacts with lysines on the antibody to form the conjugate. Titration of the conjugate against antigen-positive and antigen-negative melanoma cells indicated an inhibitory dose (ID$_{50}$) of $10^{-8}$M. In comparison, the drug verrucarol alone has an ID$_{50}$ of $10^{-5}$M or greater when tested in the same assay.

EXAMPLE II

Verrucarin A

Verrucarin A or its hemisuccinate is conjugated to monoclonal antibody 9.2.27 by the same method as stated in Example I. The verrucarin A hemisuccinate was prepared as follows: A solution of 0.375 mM trichothecene in dry CHCl$_3$ (1 ml) was mixed with 0.45 mM succinic anhydride (1.2 eqnts.) and a catalytic amount of dimethyl amino pyridine. The mixture was held at reflux overnight, diluted to 30 ml with CH$_2$Cl$_2$, and washed with 10 ml 5% av. HCl. The organic layer was dried with Na$_2$SO$_4$, concentrated, and the resulting gum subjected to preparative TLC (silica gel, 2 mm; ethyl acetate:hexane-1:1). The trichothecene hemisuccinate was recovered in 80% yield after recrystallization from CH$_2$Cl$_2$/hexane/ether. Increasing titers of the conjugate are incubated with the antigen-positive and antigen-negative melanoma cells and then tested for potency and selectivity as described herein. The ID$_{50}$ against the antigen-positive cells was $10^{-7}$M or better, while there was no toxicity against the antigen-negative cells. Verrucarin A itself yielded an ID$_{50}$ of $2.5 \times 10^{-11}$M.

EXAMPLE III

Conjugation via cis-Aconityl Linkages

Verrucarol is covalently linked to cis-aconitic anhydride using standard procedures, such as that described above for the preparation of hemisuccinate. Alternatively, the N-succinimidyl ester of verrucarol may be reacted with a diamine. The N-succinimidyl ester of verrucarol was prepared as follows: A sample of 0.068 mM Verrucarol hemisuccinate dissolved in 2 ml of tetrahydrofuran is added to 0.36 mM each of N-hydroxysuccinimide and dicyclohexyl carbodiimide. The mixture is allowed to stand at room temperature for 6 hours, filtered to remove N-N-dicyclohexyl urea and concentrated. The N-succinimidate was isolated by preparative layer chromatography using an EtAc/hexane solvent system on a silica gel plate (2 mm). Final purification was achieved by recrystallization from diethyl ether to give about 70% yield. The derivatized trichothecene ester may then be covalently linked to cis-aconitic anhydride through the free amino group. The cis-aconityl moieties of the derivatived trichothecene may then be covalently linked to antibody using a carbodiimide linking molecule, as described in Example I.

EXAMPLE IV

Glycosylation of Anguidine

Anguidine, a simple trichothecene, is poorly soluble, but glycosylation of anguidine improves solubility. Anguidine is glycosylated according to the method of W. R. Roush et al., *J. Am. Chem. Soc.* 107: 3354–3355, 1985. Briefly, anguidine (12 um) is incubated with uridine 5'-diphosphoglucuronic acid (12 mM), B-napthoflavone-induced hepatic microsomes from male rats (0.6 mg of protein/ml), MgCl$_2$ (2.5 mM), and K$_2$HPO$_4$ (10 mM, pH 7.7) at 37° C. for 3.5 hours. Using the procedure, anguidine glucuronide can be formed in approximately 60% yield. Glycosylated anguidine may then be conjugated to antibody hemisuccinate derivatives, according to Example II.

EXAMPLE V

Reduction of Intoxification

Verrucarin A-antibody conjugates are administered intravenously to a warm-blooded animal, in order to inhibit antigen-positive cells. Metabolic processes of the recipient animal may cause the premature release of the trichothecene portion of the conjugate, resulting in toxicity to cells that are not antigen-positive.

The intoxification that may result from the release of unconjugated trichothecene may be reduced by administration of anti-trichothecene antibody. Briefly, either at a predetermined time after injection of a verrucarin A-antibody conjugate, or upon detection of toxicity symptoms in a recipient, antibody capable of binding to and blocking the toxicity of verrucarin A is injected into the recipient.

Alternatively, either at a predetermined time after injection of conjugate or upon symptoms of toxicity, an intoxified recipient's plasma may be passed through an affinity column containing immobilized anti-verrucarin A antibody. The affinity column binds verrucarin A, thereby reducing the level of free verrucarin A in the plasma. The plasma is then infused back into the recipient.

EXAMPLE VI

Reduction of Gastrointestinal Levels of Verrucarin A

Injection of verrucarin A-antibody conjugates into a recipient may result in the release of free verrucarin A into the gut of the recipient. The toxicity of the released verrucarin A may be decreased through a reduction of gastrointestinal levels of the free trichothecene (as described, for example, in Buck and Bratich, *Vet. Med.* 81: 73–77, 1986). This may be accomplished by orally administering activated charcoal to an intoxified recipient. Activated charcoal binds free verrucarin A, thus preventing absorption from the gastrointestinal tract. The recipient is then given an oral cathartic, which facilitates the movement of the activated charcoal-trichothecene complexes through the gut.

From the foregoing it will be appreciated that, although specific embodiments of the invention have been described herein for purposes of illustration, various modifications may be made without deviating from the spirit and scope of the invention.

I claim:

1. A conjugate of a trichothecene and an antibody or antibody fragment that is capable of specifically binding to a defined population of cells, wherein said trichothecene is selected from the group consisting of myrotoxin A, myrotoxin B, myrotoxin C, myrotoxin D, mytoxin A, mytoxin B, mytoxin C, roritoxin A, roritoxin B, roritoxin C and roritoxin D.

2. A conjugate of a trichothecene and an antibody or antibody fragment that is capable of specifically binding to a defined population of cells wherein said trichothecene comprises the formula:

wherein:
$R_1$ is H, OH, or O—C—CH$_3$
$R_2$ is H, OH, O—C—CH$_3$, or OCOCH$_2$CH(CH$_3$)$_2$; and
R' is:

3. A conjugate of a trichothecene and an antibody or antibody fragment that is capable of specifically binding to a defined population of cells wherein said trichothecene and said antibody or antibody fragment are coupled through a covalent linkage formed between a trichothecene/poly-L-lysine complex and one or more sulfhydryl or carboxyl groups of the antibody or antibody fragment.

4. A method for producing a trichothecene conjugate with improved solubility, comprising:
glycosylating a trichothecene to form a glycosylated trichothecene; and
conjugating said glycosylated trichothecene to an antibody or antibody fragment that is capable of specifically binding to a defined population of cells, thereby forming said trichothecene conjugate.

5. A conjugate of a trichothecene and an antibody or antibody fragment that is capable of specifically binding to a defined population of cells wherein said conjugate is rendered soluble by glycosylation.

6. A method for reducing intoxification in a recipient of a conjugate of a trichothecene and an antibody or antibody fragment that is capable of specifically binding to a defined population of cells, comprising:
administering to the recipient the conjugate of a trichothecene and an antibody or antibody fragment; and
administering to the recipient monoclonal or polyclonal antibodies that inhibit the toxicity of released trichothecene.

7. A method for reducing intoxification in a recipient of a conjugate of a trichothecene and an antibody or antibody fragment that is capable of specifically binding to a defined population of cells, comprising:
administering to the recipient the conjugate of a trichothecene and an antibody or antibody fragment; and
administering to the recipient activated charcoal and an oral cathartic, thereby reducing gastrointestinal levels of free trichothecene.

* * * * *